US00PP09270P

United States Patent [19]

Archer

[11] Patent Number: Plant 9,270

[45] Date of Patent: Aug. 29, 1995

[54] VERBENA PLANT 'L. ARCHER'

[75] Inventor: Lenzie Archer, Thomson, Ga.

[73] Assignee: McCorkle Nursery Inc., Dearing, Ga.

[21] Appl. No.: 265,469

[22] Filed: Jun. 24, 1994

[51] Int. Cl.[6] ..... A01H 5/00

[52] U.S. Cl. ..... Plt./87

[58] Field of Search ..... Plt. 87

*Primary Examiner*—James R. Feyrer

*Attorney, Agent, or Firm*—Henderson & Sturm

[57] ABSTRACT

A new variety of *Verbena*×*hybrida* is provided. The plant has rapid growth, particularly under nursery conditions, the habit is densely spreading, resulting from the many branches, multiple breaks from the new shoots and short internodes, and the flower is a deep red-rose color.

2 Drawing Sheets

SUMMARY OF THE INVENTION

This invention relates to a new and distinct variety of *Verbena*×*hybrida* cultivar which is outstanding because of its deep red-rose flower color, cold hardiness, rapid growth, dense plant habit, and free and basal branching characteristics being so selected from a planting of a mixture of *Verbena*×*hybrida*being grown in McDuffie County, Ga. in a cultivated area.

ORIGIN AND ASEXUAL REPRODUCTION

Asexual reproduction of this cultivar by rooted cuttings was directed by me, such reproduction establishing that the plant does in fact maintain the characteristics described, in successive generations.

It should be noted that the plant was initailly selected where grown in or near McDuffie County, Ga. and has since been asexually reproduced in the vicinity of Dearing, Ga. with the characteristics stated, found to be maintained through successive generations as before recited.

The cultivar may further be described as having a number of distinctive characteristics whcih are enumerated in the succeeding specific description but broadly stated as comprising a new *Verbena*×*hybrida* cultivar which has rapid growth, particularly under nursery conditions and where rooted cuttings reach saleable size in a one-gallon container in approximately twelve weeks. This *Verbena*×*hybrida* has a distinct deep red-rose flower color and a densely spreading habit resulting from the many branches, multiple breaks from the new shoots and short internodes. It typically forms a mount 1 feet in height and 5–6 feet in diameter in one growing season when grown in ordinary garden soil in the area of Dearing, Ga.

I have chosen to identify this new cultivar as *Verbena*×*hybrida* "L. Archer".

It is possible that other identification will be adopted in the trade, but the name selected will serve for the purposes hereof.

BRIEF DESCRIPTION OF THE PHOTOGRAPHS

The accompanying photographs show as nearly as true as it is reasonably possible to make the same, in a color illustration of this character, typical specimens of the plant parts of the new variety. The plants of the new variety were approximately three months from cutting propagation.

In the photographs:

FIG. 1 discloses the new variety;
FIG. 2 illustrates the mature flower;
FIG. 3 illustrates the top of mature leaves; and
FIG. 4 illustrates the bottom of mature leaves.

DETAILED DESCRIPTION

Figure 1:
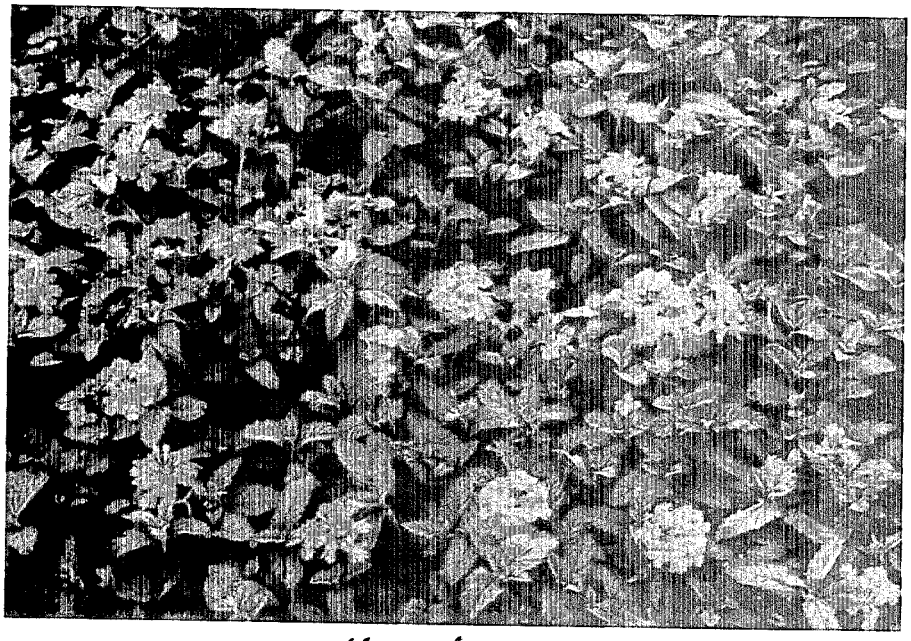
Figure 2:
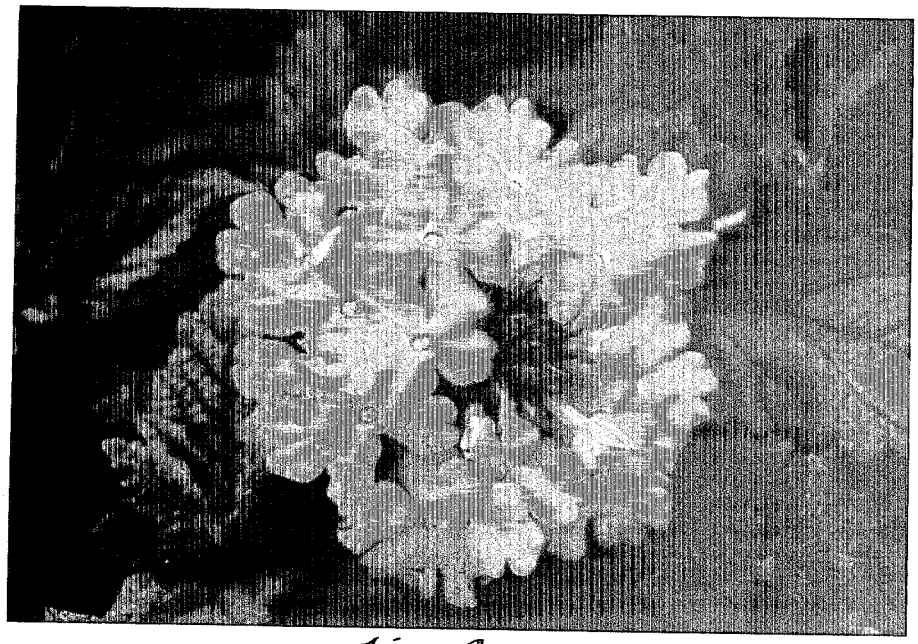
Figure 3:
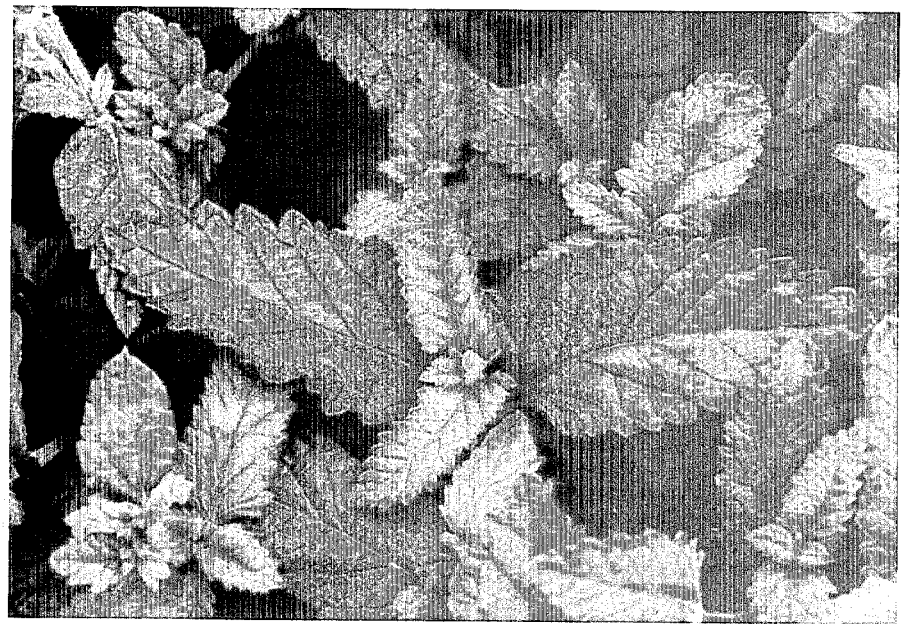
Figure 4:
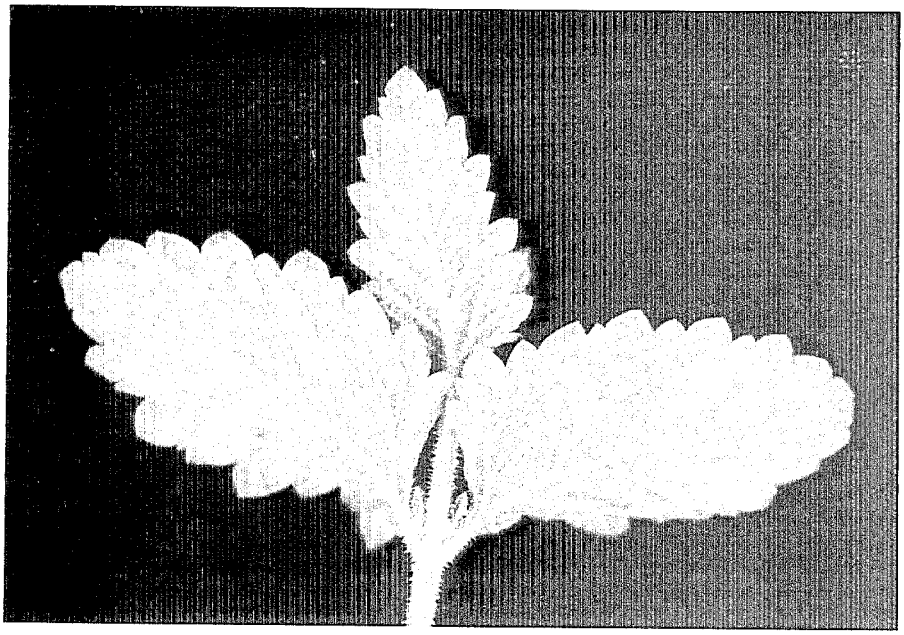

In order to more specifically identify the cultivar descriptive details are set forth hereinafter, along with related aspects of the plant which serve to distinguish the same, all colors being noted as compared with The Royal Horticultural Society Colour Chart. The measurements and colors were recorded fron the mature plants grown in 6 inch diameter pots in the vicinity of Dearing, Ga. Three fully developed units of each organ type were measured from each plant. Leaves penultimate to leaves subtending flowers were selected for measurement.

Parentage:

*Origin.*—This new cultivar was selected in rural McDuffie County, Ga. on the homestead of Lenzie Archer in a cultured planting of *Verbena*×*hybrida.* The planting resulted from a purchase of several seedling annual *Verbena*×*hybrida* bedding plants from a local garden center no longer in business. With the advent of winter the other plants were killed by cold weather. Only *Verbena*×*hybrida* "L. Archer" overwintered successfully and has proved to be perennial. These hybrid garden *Verbena*×*hybridas* typically result from complex parentage involving *Verbena incisa, Verbena peruviana, Verbena phlogiflora,* and *Verbena teucroides.*

General: A trailing perennial herb with tetragonal stems, softly pubescent in all parts, spreading to 5 to 6 feet in a single growing season.

Propagation: Plant cuttings started near Dearing, Ga.

Plant Descriptions:

*Plant Height.*—Approximately 12 inches.

*Petioles.*—Average 0.25 inches in length, pubescent.

*Leaves.*—The mature leaf is toothed, ovate to ovate-oblong rugose, pubescent below especially along midvein, less pubescent above, and measures an average of 2.5 inches long by 1.5 inches wide.

*Color.*—The upper leaf surface is dark green (RHS 136A) and the lower leaf surface is light green (RHS 137B).

*Stems.*—Covered with soft pubescence, creeping to ascending in habit and rooting at the nodes when contacting the soil surface.

Flower:

*Type.*—The flowers are held in spikes. The width of the inflorescence is 2¼". Each individual flower is ¾'⅞" in width and 1" in length with 5/16" of that length being above the calyx.

*Flowers are produced beginning in early spring, throughout summer and fall, and even during mild winter weather.*

*Color.*—The color of the flowers is a very distinct deep rose-red (RHS 45B).

*Fruit.*—The flowers and fruit are similar in shape but differ in color and density. Fruit is dry and enclosed in calyx. Structure is same as inflorescence. *Verbena*×*hybrida* "L. Archer" has been grown in monoculture for 3 years without producing a seedling.

*Diseases.*—No unusual susceptability to diseases noted to date.

*Insects.*—No unusual susceptability to insects noted to date.

*Cold hardiness.*—*Verbena*×*hybrida* cultivars are listed in as cold hardy to Zone 9 in the Royal Horticultural Society Dictionary of Gardening. In tests conducted by Dr. Orville Lindstrom of the University of Georgia Extension Horticulture Department the above-ground tissues of *Verbena*×*hybrida* "L. Archer" were found to be hardy to 7 degrees Fahrenheit. In addition when grown in containers adjacent to *Verbena*×*hybrida* "Abbeville", Abbeville was killed by ambient temperatures of 8 degrees Fahrenheit and *Verbena*×*hybrida* "L. Archer" survived undamaged. When grown in a garden adjacent to *Verbena*×*hybrida* "Carousel" and "Silver Ann", *Verbena*×*hybrida* "L. Archer" survived the winter in an evergreen condition while the two former cultivars died. Dr. Lindstrom's research finds the cold hardiness of *Verbena*×*hybrida* "L. Archer" to be comparable to that of *Verbena* "Homestead Purple".

General Observations: The color of the flower and cold hardiness distinguish this variety from other commercially available *Verbena*×*hybrida* cultivars.

The cultivar may be compared with known varieties along the following lines where observation were made on plants grown under similar conditions near Dearing, Ga.

*Verbena canadensis* "Evelyn Scott" has shorter, narrower leaves and a rose flower color while "L. Archer" has a deep red-rose flower color and longer, broader leaves.

*Verbena canadensis* "Homestead Purple" has a purple flower color while "L. Archer" has a deep red-rose flower color.

*Verbena*×*hybrida* "Carrousel" has a white and purple flower color while "L. Archer" has a deep red-rose flower color. "Carousel" was killed at 7 degrees Fahrenheit which did no harm to "L. Archer".

*Verbena*×*hybrida* "Pink Parfait" has a pink with white flower color while "L. Archer" has a deep red-rose flower color.

*Verbena*×*hybrida* "Defiance" is deep red in color but is hardy only to Zone 9. "L. Archer" is hardy to Zone 6.

I claim:

1. A new and distinct cultivar of *Verbena*×*hybrida* substantially as described and illustrated herein, characterized particularly as to novelty by its deep red-rose flower color, cold hardiness, rapid, particularly under nursery conditions, and free and basal branching providing a cultivar well suited as a flowering pot plant having no unusual susceptability to the traditional *Verbena*×*hybrida* diseases and insects.

* * * * *